United States Patent
Carr et al.

[11] 3,946,022
[45]*Mar. 23, 1976

[54] PIPERIDINE DERIVATIVES

[75] Inventors: Albert A. Carr; C. Richard Kinsolving, both of Cincinnati, Ohio

[73] Assignee: Richardson-Merrell Inc., Wilton, Conn.

[ * ] Notice: The portion of the term of this patent subsequent to Apr. 23, 1991, has been disclaimed.

[22] Filed: Mar. 4, 1974

[21] Appl. No.: 447,926

[52] U.S. Cl. 260/293.64; 260/247.5 G; 260/268 PH; 260/293.62; 260/293.68; 260/293.71; 260/293.78; 260/293.79; 260/293.8; 260/293.83; 260/293.84; 424/248; 424/250; 424/267

[51] Int. Cl.[2]................................. C07D 211/22

[58] Field of Search . 260/247.5 G, 268 PH, 293.64, 260/293.71, 293.78, 293.79, 293.8, 293.83, 293.84

[56] References Cited
UNITED STATES PATENTS

| | | | |
|---|---|---|---|
| 3,806,526 | 4/1974 | Carr et al. | 260/293.79 |
| 3,829,433 | 8/1974 | Carr et al. | 260/293.79 |

*Primary Examiner*—Sherman D. Winters
*Attorney, Agent, or Firm*—L. Ruth Hattan; Eugene O. Retter; George W. Rauchfuss, Jr.

[57] ABSTRACT

Compounds of the following general formula are useful as antihistamine agents, antiallergy agents and bronchodilators:

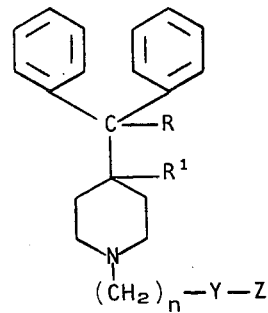

wherein R represents hydrogen or hydroxy; $R^1$ represents hydrogen; or R and $R^1$ taken together form a second bond between the carbon atoms bearing R and $R^1$; $n$ is the integer 4 or 5; Y represents

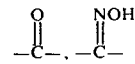

or

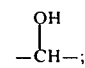

Z represents phenyl or a substituted phenyl ring wherein the substituent on the substituted phenyl ring is attached at the ortho, meta, or para position of the phenyl ring and is selected from halogen, a straight or branched alkyl group of from 1 to 6 carbon atoms, alkoxy of from 1 to 6 carbon atoms, cycloalkyl of from 3 to 6 carbon atoms, di(lower)alkylamino, or a saturated monocyclic heterocyclic group selected from pyrrolidino, piperidino, morpholino or N-(lower)alkyl-piperazino; and pharmaceutically acceptable acid addition salts and individual optical isomers.

19 Claims, No Drawings

PIPERIDINE DERIVATIVES

Field of Invention

This invention relates to novel compounds and their use as antihistamine agents.

Background of Invention

Compounds which may be represented by the following formula are described as antihistamine agents, antiallergy agents and bronchodilators in Belgian Pat. Nos. 794,595, 794,596, 794,597 and 794,598 which correspond respectively to copending U.S. Application Ser. No. 221,823, filed Jan. 28, 1972, now U.S. Pat. No. 3,806,526, 221,822 filed Jan. 28, 1972, now U.S. Pat. No. 3,829,433, 378,561 filed July 12, 1973 which is a continuation-in-part of U.S. application Ser. No. 221,821 filed Jan. 28, 1972 now abandoned and 221,820 filed Jan. 28, 1972.

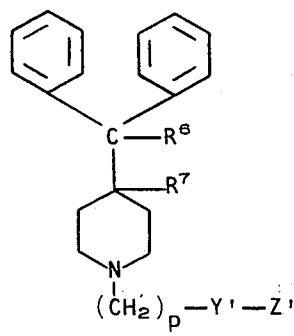

wherein $R^6$ represents hydrogen or hydroxy; $R^7$ represents hydrogen; or $R^6$ and $R^7$ taken together form a second bond between the carbon atoms bearing $R^6$ and $R^7$; p is an integer of from 1 to 3; Y' represents

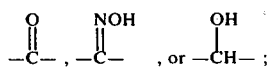

Z' represents thienyl, phenyl or substituted phenyl wherein the substituent on the substituted phenyl may be attached at the ortho, meta, or para position of the phenyl ring and is selected from halogen, a straight or branched lower alkyl chain of from 1 to 4 carbon atoms, a lower alkoxy group of from 1 to 4 carbon atoms, di(lower) alkylamino, or a saturated monocyclic heterocyclic group such as pyrrolidino, piperidino, morpholino or N-(lower)alkylpiperazino; and pharmaceutically acceptable acid addition salts and individual optical isomers.

Additionally compounds of the above formula wherein Y' is

or

and Z' is naphthyl or substituted phenyl wherein the substituent on the substituted phenyl is straight or branched alkyl of 5 or 6 carbon atoms, alkoxy of 5 or 6 carbon atoms, or cycloalkyl of 3 to 6 carbon atoms attached at the ortho, meta, or para position of the phenyl ring are disclosed as antihistamine agents, antiallergy agents and bronchodilators in copending U.S. application Ser. No. 440,855, filed Feb. 8, 1974 and Ser. No. 440,856, filed Feb. 8, 1974.

The compounds of the present invention are distinguishable over the above-cited U.S. applications in that the alkylene chain between the piperidine ring and the functional group as represented by Y in the compounds of the present invention is longer, containing 4 or 5 carbon atoms, resulting in compounds with unexpected superior utility.

Summary of Invention

The novel substituted piperidine derivatives of this invention are useful as antihistamines, antiallergy agents and bronchodilators and are represented by the formula

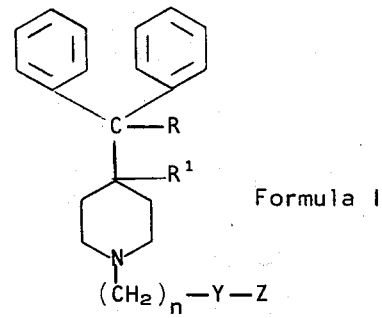

Formula I wherein R represents hydrogen or hydroxy; $R^1$ represents hydrogen; or R and $R^1$ taken together form a second bond between the carbon atoms bearing R and $R^1$; n is the integer 4 or 5; Y represents

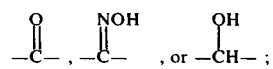

Z represents phenyl or a substituted phenyl ring wherein the substituent on the substituted phenyl ring is attached at the ortho, meta or para position of the phenyl ring and is selected from halogen, a straight or branched alkyl group of from 1 to 6 carbon atoms, an alkoxy group of from 1 to 6 carbon atoms, a cycloalkyl group of from 3 to 6 carbon atoms, a di(lower)alkylamino group, or a saturated monocyclic heterocyclic group selected from pyrrolidino, piperidino, morpholino, or N-(lower)alkylpiperazino. Pharmaceutically acceptable acid addition salts and individual optical isomers of compounds of Formula I are also included in the scope of this invention.

DETAILED DESCRIPTION OF INVENTION

Compounds of this invention are 4-substituted-piperidinoalkanone derivatives, 4-substituted-piperidinoalkanone oxime derivatives, or 4-substituted piperidinoalkanol derivatives as further represented by the following respective Formulas II to IV.

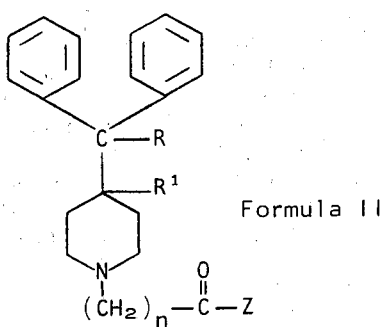

Formula II

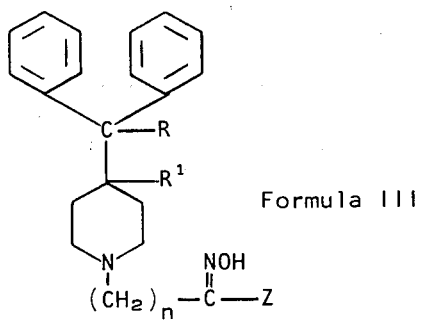

Formula III

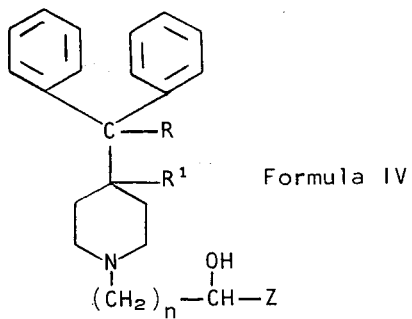

Formula IV

In the above Formulas II to IV the substituent groups as represented by R, R¹, n and Z have the meanings defined in Formula I.

The substituent on the substituted phenyl ring as represented by Z in Formulas I to IV may be attached at the ortho, meta, or para position of the phenyl ring and is selected from halogen, for example, chlorine, fluorine, bromine, iodine, preferably chlorine or fluorine; a straight or branched alkyl group of from 1 to 6 carbon atoms, for example, methyl, ethyl, n-propyl, isopropyl, n-butyl, isobutyl, tert-butyl, n-pentyl, neopentyl, and n-hexyl; an alkoxy group of from 1 to 6 carbon atoms, for example, methoxy, ethoxy, propoxy, butoxy, pentoxy, and hexyloxy; a cycloalkyl group of from 3 to 6 carbon atoms, for example, cyclopropyl, cyclobutyl, cyclopentyl, and cyclohexyl; di(lower)alkylamaino wherein the (lower)alkyl contains from 1 to 4 carbon atoms and may be straight or branched, for example, methyl, ethyl, n-propyl, isopropyl, n-butyl and tert-butyl; or a saturated monocyclic heterocyclic group such as pyrrolidino, pipereidino, morpholino or N-(lower)alkylpiperazino wherein the (lower)alkyl group contains from 1 to 4 carbon atoms and may be straight or branched, for example, methyl, ethyl, n-propyl, isopropyl, n-butyl, isobutyl, and tert-butyl.

Preferred compounds of this invention are those wherein Y is

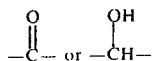

and of these compounds those wherein R is hydroxy or R and R¹ taken together form a second bond between the carbon atoms bearing R and R¹ are more preferred.

This invention also includes the pharmaceutically acceptable acid addition salts of the compounds of the hereinbefore set forth formulas, optical isomers and salts thereof. Pharmaceutically acceptable acid addition salts of the compounds of this invention are those of any suitable inorganic or organic acid. Illustrative examples of suitable inorganic acids are hydrochloric, hydrobromic, sulphuric, and phosphoric acids. Illustrative examples of suitable organic acids include carboxylic acids, such as, acetic, propionic, glycolic, lactic, pyruvic, malonic, succinic, fumaric, malic, tartaric, citric, ascorbic, maleic, hydroxymaleic, and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, and mandelic acid; and sulfonic acids, such as, methanesulfonic, ethanesulfonic, and β-hydroxyethanesulfonic acid.

Illustrative examples of compounds of this invention are 4-(α,α-diphenylmethyl)-α-(p-N-methylpiperazinophenyl)-1-piperidinehexanol, 4-(α,α-diphenylmethylene)-α-(p-cyclobutylphenyl)-1-piperidinepentanol, 4-(α-hydroxy-α-phenylbenzyl)-α-(p-ethoxyphenyl)-1-piperidinepentanol, 4-(α,α-diphenylmethyl)-α-(p-chlorophenyl)-1-piperidinehexanol, 5-[4-(α-hydroxy-α-phenylbenzyl)piperidino]-4'-bromovalerophenone, 6-[4-(α-hydroxy-α-phenylbenzyl)piperidino]caprophenone, 5-[4-(α,α-diphenylmethyl)piperidino]-4'-morpholinovalerophenone, 4'-dimethylamino-6-[4-(α,α-diphenylmethylene)piperidino]caprophenone, 6-[4-(α,α-diphenylmethyl)piperidino]caprophenone oxime, 5-[4-(α, α-diphenylmethylene)piperidino]-4'-isopropylvalerophenone oxime, 4'-ethyl-6-[4-(α-hydroxy-α-phenylbenzyl)piperidino]caprophenone, 6-[4-(α-hydroxy-α-phenylbenzyl)piperidino]-4'-neopentylcaprophenone, 5-[4-(α,α-diphenylmethyl)-piperidino]-4'-hexyloxyvalerophenone, and 5-[4-(α-hydroxy-α-phenylbenzyl)piperidino]-4'-piperidinovalerophenone.

The novel compounds of this invention are useful as antihistamines, antiallergy agents and bronchodilators, and are further characterized by minimal central nervous system stimulant and depressant effects which are commonly found in commercial antihistamines. The compounds may be administered alone or with suitable pharmaceutical carriers to warm blooded animals, mammals such as felines, canines, porcine, bovine, equine, and humans and can be in solid or liquid form such as, for example tablets, capsules, powders, solutions, suspensions, or emulsions.

The compounds of this invention can be administered orally, parenterally, for example, subcutaneously, intravenously, intramuscularly, intraperitoneally, by intranasal instillation or by application to mucous membranes such as that of the nose, throat, and bronchial tubes, for example, in an aerosol spray containing small particles of a compound of this invention in a spray or dry powder form.

The quantity of novel compounds administered will vary. Depending on the patient and the mode of administration, the quantity of novel compound administered may vary over a wide range to provide in a unit dosage of from about 0.01 to 15 milligrams per kilogram of body weight of the patient per dose to achieve the desired effect. For example the desired antihistamine, antiallergy and bronchodilator effects can be obtained by consumption of a unit dosage form such as, for example, a tablet containing 1 to 40 milligrams of a novel compound of this invention taken 1 to 4 times daily.

The solid unit dosage forms can be of the conventional type. Thus, the solid form can be a capsule which can be of the ordinary gelatin type containing a novel compound of this invention and a carrier, for example, lubricant and inert fillers such as lactose, sucrose, corn starch, and the like. In another embodiment, the novel compounds are tabletted with conventional tablet bases such as lactose, sucrose, corn starch, and the like in combination with binders such as acacia, corn starch or gelatin, disintegrating agents such as corn starch, potato starch, or alginic acid, and a lubricant such as stearic acid, or magnesium stearate.

The novel compounds may also be administered as injectable dosages by solution or suspension of the compounds in a physiologically acceptable diluent with a pharmaceutical carrier which can be a sterile liquid such as water and/or oils, with or without the addition of a surfactant and other pharmaceutically acceptable adjuvants. Illustrative of oils there can be mentioned those of petroleum, animal, vegetable or synthetic origin, for example, peanut oil, soybean oil, mineral oil, and the like. Water, saline, aqueous dextrose, and related sugar solutions, ethanols and glycols such as propylene glycol or polyethylene glycol are illustrative of liquid carriers for injectable solutions.

For use as aerosols the novel compounds in solution or suspension may be packaged in a pressurized aerosol container together with a gaseous or liquified propellant, for example, dichlorodifluoromethane, dichlrodifluoromethane with dichlorodifluoroethane, carbon dioxide, nitrogen, propane, etc. with the usual adjuvants such as co-solvents, and wetting agents, as may be necessary or desirable. The compounds may also be administered in a non-pressurized form such as in a nebulizer or atomizer.

The compounds of this invention possess unexpected superior utility as antihistamine agents compared to the corresponding lower homologs. To illustrate the utility of the compounds of this invention the following tabulation indicates the amount of certain representative compounds of this invention required to reduce by 50% wheals induced by intradermal injection of 1γ of histamine into guinea pigs as compared to the direct lower homolog. Each compound was orally administered one hour prior to the histamine injection.

| Compound of invention | $ED_{50}$ mg/kg |
|---|---|
| 4'-fluoro-5-[4-(α-hydroxy-α-phenylbenzyl)piperidino]-valerophenone hydrochloride | 0.8 |
| 5-[4-(α-hydroxy-α-phenylbenzyl)piperidino]valerophenone hydrochloride | 0.7 |
| Lower homologs | |
| 4'-fluoro-4-[4-(α-hydroxy-α-phenylbenzyl)piperidino]-butyrophenone hydrochloride | 3.5 |
| 4-[4-(α-hydroxy-α-phenylbenzyl)piperidino]butyrophenone hydrochloride | 6.1 |

The compounds of this invention may be prepared by several methods, and some of the compounds of this invention are used to prepare other compounds of the invention as will be apparent from the following.

The compounds of Formula I wherein Y represents

may be prepared by reacting a 4-substituted piperidine, compound 1, with an ω-haloalkyl aryl ketone, compound 2, as indicated by the following:

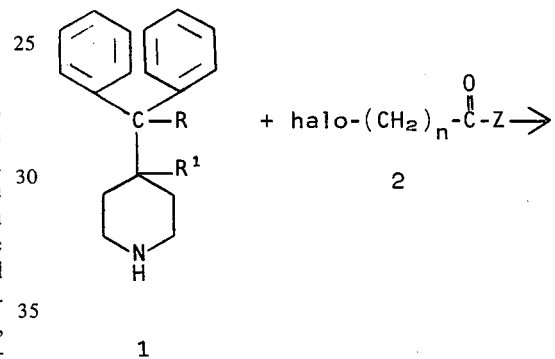

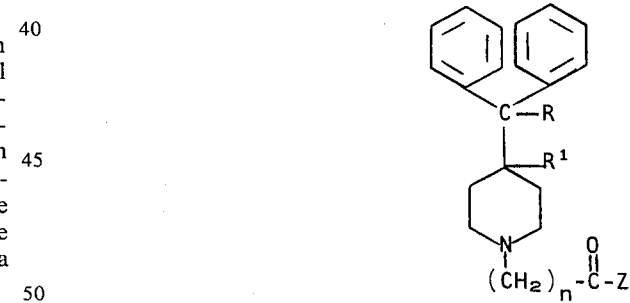

Formula II

In the above reaction halo represents a reactive halogen atom, and R, $R^1$, n, and Z have the meanings defined in general Formula I.

The above reaction is carried out in alcoholic solvents, such as, methanol, ethanol, isopropyl alcohol, and n-butanol; in ketone solvents, such as, butanone, and methyl isobutyl ketone; in hydrocarbon solvents such as benzene and toluene; or in halogenated hydrocarbons, such as, chlorobenzene; in the presence of an inorganic base such as sodium bicarbonate or potassium carbonate, or in the presence of an organic base such as triethylamine, or an excess of compound 1. In some cases it may be desirable to add catalytic amounts of potassium iodide to the reaction mixture. The reaction time is usually about 48 hours, but may vary from about 4 to 175 hours at a temperature of from about 70°C to the reflux temperature of the solvent.

The ω-haloalkyl aryl ketone derivatives, compound 2, may be prepared by reacting the appropriate ω-haloalkanoyl halide and an aromatic compound in the presence of aluminum choride. They may also be prepared by reacting a substituted phenyl Grignard reagent with an ω-haloalkanonitrile, followed by the usual work up.

The 4-diphenylmethylpiperidine and α,α-diphenyl-4-piperidinemethanol starting materials as represented by compound 1 wherein R is hydrogen or hydroxy, and $R^1$ is hydrogen are commercially available. 4-Diphenylmethylenepiperidine as represented by compound 1 wherein R and $R^1$ form a second bond between the carbon atoms bearing R and $R^1$ may be prepared by dehydration of α,α-diphenyl-4-piperidinemethanol by generally known procedures.

The compounds of Formula I wherein Y represents

may also be prepared by the reaction of an appropriately 4-substituted 1-piperidinealkanonitrile with an organometallic compound such as in an aryl Grignard or an aryllithium compound in a solvent such as diethyl ether or tetrahydrofuran followed by isolation and purification of the aryl 4-substituted piperidinoalkyl ketone derivative by generally known procedures. The nitrile derivative is obtained by the reaction of an appropriately subsituted piperidine compound with a haloalkylnitrile.

The compounds of Formula I wherein Y represents

and Z represents a substituted phenyl wherein the substituent on the substituted phenyl is selected from a di(lower)alkylamino group or a saturated monocyclic heterocyclic group and is attached at the ortho or para position of the phenyl ring may also be prepared from the corresponding halogen substituted phenyl derivative, preferably a fluoro derivative, using an excess of the dialkylamine or the heterocyclic amine. When volatile amines are employed the amine may be bubbled through a solution of the halogen substituted phenyl derivative in dimethylsulfoxide at about 100°C for about 4 to 8 hours. When higher boiling amines are employed such as, for example, piperidine, excess amounts of the amine are used as base, reactant, and solvent for the reaction which is carried out at the reflux temperature of the amine for about 4 to 24 hours.

The compounds of general Formula I wherein Y represents

may be prepared by the addition of a hydroxylamine salt to the corresponding aryl 4-substituted-piperidinoalkyl ketone, that is, compounds of general Formula I wherein Y represents

as represented by the following:

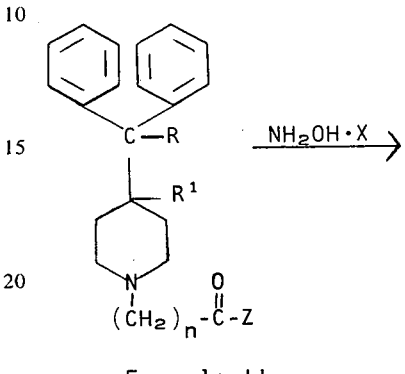

Formula II

Formula III

In the above reaction R, $R^1$, n and Z have the meanings defined in general Formula I, and $NH_2OH \cdot X$ represents an acid addition salt of hydroxylamine.

The above reaction may be carried out in lower alcoholic solvents or water, or a combination of a lower alcoholic solvent and water in the presence of a mineral base such as sodium hydroxide, potassium hydroxide, or sodium acetate, or an organic base such as pyridine. The reaction time varies from about 1 to 8 hours, and the reaction temperature varies up to 100°C. Depending on the amount of base used, the strength of the base used and/or the method employed to isolate the product as represented by Formula III, the product is obtained as the free base or the acid addition salt as is exemplified in the specific examples.

The compounds of general Formula I wherein Y represents $$\begin{array}{c} OH \\ | \\ -CH- \end{array}$$

may be prepared by reducing the corresponding aryl 4-substituted-piperidinoalkyl ketone, that is, compounds of general Formula I wherein Y represents

as illustrated below:

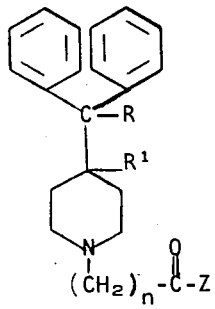

Formula II

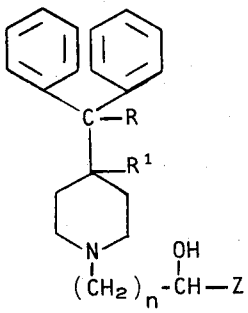

Formula IV

In the above reaction R, R¹, n and Z have the meanings defined in general Formula I.

Preferred reducing agents such as sodium borohydride may be employed in the above reaction using a lower alcohol solvent such as methanol, isopropyl alcohol, and tertbutanol. The reaction is carried out at temperatures ranging from about 0°C to the reflux temperature of the solvent, and the reaction time varies from about 0.5 to about 8 hours. Other hydrides as reducing agents such as lithium aluminum hydride and diborane may also be used in an appropriate solvent such as diethyl ether.

This reaction may also be achieved by catalytic reduction using Raney nickel, palladium, platinum or rhodium catalysts in lower alcohol solvents, acetic acid, or their aqueous mixtures, or by aluminum isopoxide in isopropanol.

The aryl 4-substituted-piperidinoalkyl ketone derivatives as represented by Formula II in the above two reactions may be prepared by methods described hereinbefore.

The optical isomers of the compounds of this invention may be separated by using a (+) or (−) binaphthylphosphoric acid derivative or a salt of said derivative and an assymetric base by the method described by R. Viterbo et al., in Tetrahedron Letters No. 48, pp. 4617–4620 (1971).

EXAMPLE 1

4'-tert-Butyl-5-[4-(α-hydroxy-α-phenylbenzyl)-piperidino]valerophenone hydrochloride A mixture of 32.0 g (0.12 mole) of α,α-diphenyl-4-piperidinemethanol, 38.0 g (0.15 mole) of 4'-tert-butyl-5-chlorovalerophenone, 27.8 g (0.2 mole) of potassium bicarbonate, and 200 mg of potassium iodide in about 500 ml of toluene is stirred and refluxed for 142 hours then filtered while hot. About 50 ml of ether is added to the filtrate which is then made acidic using ethereal HCl. The resulting precipitate is recrystallized from methanol-butanone to give 4'-tert-butyl-5-[4-(α-hydroxy-α-phenylbenzyl)piperidino]-valerophenone hydrochloride, M.P. 209.5°–211°C.

EXAMPLE 2

4'-Fluoro-5-[4-(α-hydroxy-α-phenylbenzyl)-piperidino]valerophenone hydrochloride A mixture of 19.3 g (0.07 mole) of α,α-diphenyl-4-piperidinemethanol, 17.1 g (0.08 mole) of 5-chloro-4'-fluorovalerophenone, 20.0 g (0.2 mole) of potassium bicarbonate, and 0.1 g of potassium iodide in 250 ml of toluene and 35 ml of water is stirred on a steam bath for 70 hours. The organic layer is separated and combined with two 50 ml toluene extracts of the aqueous layer. The combined organic material is washed with water and saturated sodium chloride solution, dried over magnesium sulfate and filtered. The filtrate is diluted with about 200 ml of ether then made acidic with ethereal HCl. The resulting precipitate is recrystallized from methanol-butanone to give 4'-fluoro-5-[4-(α-hydroxy-α-phenylbenzyl)piperidino]valerophenone hydrochloride, M.P. 177°–179°C.

EXAMPLE 3

5-[4-(α-Hydroxy-α-phenylbenzyl)piperidino]-4'-methoxyvalerophenone hydrochloride A mixture of 41.5 g (0.15 mole) of α,α-diphenyl-4-piperidinemethanol, 38.6 g (0.17 mole) of 5-chloro-4'-methoxyvalerophenone, 30 g of potassium bicarbonate, and 0.19 g of potassium iodide in 500 ml of toluene and 70 ml of water is stirred and refluxed for 136 hours. The organic layer is separated and combined with toluene extracts of the aqueous layer. The combined organic material is washed with water and saturated sodium chloride solution, dried over magnesium sulfate and filtered. The filtrate is diluted with ether and made acidic with ethereal HCl. The resulting precipitate is recrystallized from methanol-butanone to give 5-[4-(α-hydroxy-α-phenylbenzyl)piperidino]-4'-methoxyvalerophenone hydrochloride, M.P. 211°–213°C.

EXAMPLE 4

5-[4-(α-Hydroxy-α-phenylbenzyl)piperidino]-valerophenone hydrochloride

A mixture of 27.6 g (0.1 mole) of α,α-diphenyl-4-piperidinemethanol, 21.6 g (0.11 mole) of 5-chlorovalerophenone, 20 g of potassium bicarbonate, and 0.1 g of potassium iodide in 300 ml of toluene and 25 ml of water is stirred and refluxed for 136 hours then worked up by the procedure described in Examples 2 and 3 to give 5-[4-(α-hydroxy-α-phenylbenzyl)-piperidino]valerophenone hydrochloride, M.P. 162°–164°C.

EXAMPLE 5

4'-tert-Butyl-6-[4-(α-hydroxy-α-phenylbenzyl)-piperidino]caprophenone hydrochloride A mixture of 22.4 g (0.08 mole) of α,α-diphenyl-4-piperidinemethanol, 23.8 g (0.09 mole) of 4'-tert-butyl-6-chlorocaprophenone, 20 g (0.2 mole) of potassium bicarbonate, 0.1 g of potassium iodide in 300 ml of toluene and 45 ml of water is stirred on a steam bath for about 96 hours after which the organic layer is separated and combined with toluene extracts of the aqueous layer. The combined organic material is washed with water and saturated sodium chloride solution, dried over magnesium sulfate, and filtered. The filtrate is diluted with ether and made acidic with ethereal HCl. The resulting precipitate is recrystallized from methanol-butanone to give 4'-tert-butyl-6-[4-(α-hydroxy-α-phenylbenzyl)piperidino]caprophenone hydrochloride.

EXAMPLE 6

4'-tert-Butyl-6-[4-(α,α-diphenylmethylene)-piperidino]caprophenone hydrochloride A mixture of 20.0 g (0.08 mole) of 4-(α,α-diphenylmethylene)piperidine, 23.8 g (0.09 mole) of 4'-tert-butyl-6-chlorocaprophenone, 20 g of potassium carbonate, and 0.1 g of potassium iodide in 300 ml of toluene and 45 ml of water is stirred on a steam bath for about 96 hours and worked up by the procedure described in Example 5 to give 4'-tert-butyl-6-[4-(α,α-diphenylmethylene)piperidino]caprophenone hydrochloride.

EXAMPLE 7

6-[4-(α-Hydroxy-α-phenylbenzyl)piperidino]-4'-methoxycaprophenone hydrochloride

A mixture of 27.6 g (0.1 mole) of α,α-diphenyl-4-piperidinemethanol, 26.5 g (0.11 mole) of 6-chloro-4'-methoxycaprophenone, 20 g of potassium bicarbonate, and 0.1 g of potassium iodide in 300 ml of toluene and 45 ml of water is stirred on a steam bath for about 82 hours then worked up by the procedure described in Example 5 to give 6-[4-(α-hydroxy-α-phenylbenzyl)piperidino]-4'-methoxycaprophenone hydrochloride.

EXAMPLE 8

When in the procedure of Example 2 appropriate amounts of the 4-substituted piperidine and haloalkyl aryl ketone each listed below are substituted respectively for α,α-diphenyl-4-piperidinemethanol and 5-chloro-4'-fluorovalerophenone, the respective products listed below are obtained.

EXAMPLE 9

α-(p-tert-Butylphenyl)-4-(α-hydroxy-α-phenylbenzyl)-1-piperidinepentanol

A. To 62.3 g (0.12 mole) of 4'-tert-butyl-5-[4-(α-hydroxy-α-phenylbenzyl)piperidino]valerophenone hydrochloride dissolved in about 1200 ml of methanol is added methanolic potassium hydroxide until the solution is basic. The solution is cooled in an ice bath with stirring and 5 g (0.13 mole) of sodium borohydride is added portionwise. The mixture is stirred an additional half hour, allowed to warm to room temperature then heated on a steam bath for half an hour. The solvent is removed at reduced pressure and the remaining residue is washed with water and recrystallized from acetone to give α-(p-tert-butylphenyl)-4-(α-hydroxy-α-phenylbenzyl)-1-piperidine-pentanol.

B. The title compound may also be prepared by reducing the corresponding valerophenone derivative dissolved in methanol at 2 atmospheres of hydrogen pressure in the presence of rhodium on charcoal catalyst for about 3 hours. Following the reduction reaction the catalyst is removed by filtration, and the remaining material is concentrated to a solid which is purified by recrystallization to give α-(p-tert-butylphenyl)-4-(α-hydroxy-α-phenylbenzyl)-1-piperidinepentanol as the hydrochloride.

EXAMPLE 10

When in the procedure of Example 9 an appropriate amount of the compounds of Examples 2 through 8 is respectively substituted for 4'-tert-butyl-5-[4-(α-hydroxy-α-phenylbenzyl)piperidino]valerophenone hydrochloride, the following compounds are obtained.

α-(p-fluorophenyl)-4-(α-hydroxy-α-phenylbenzyl)-1-piperidinepentanol,

α-(p-anisyl)-4-(α-hydroxy-α-phenylbenzyl)-1-piperidinepentanol, 4-(α-hydroxy-α-phenylbenzyl)-1-piperidinepentanol, α-(p-tert-butylphenyl)-4-(α-hydroxy-α-phenylbenzyl)-1-piperidinehexanol, α-(p-tert-butylphenyl)-4-(α,α-diphenylmethylene)-1-piperidinehexanol, α-(p-anisyl)-4-(α-hydroxy-α-phenylbenzyl)-1-piperidinehexanol, 4-(α,α-diphenylmethyl)-α-(p-tolyl)-1-piperidinepentanol, 4-(α,α-diphenylmethyl)α-(p-n-pentoxyphenyl)-1-piperidinehexanol, α-(p-dimethylaminophenyl)-4-(α,α-diphenylmethylene)-1-piperidinepentanol, and

| 4-Substituted piperidine | Alkyl aryl ketone | Product |
| --- | --- | --- |
| 4-(α,α-diphenylmethyl)piperidine | 5-chloro-4'-methylvalerophenone | 5-[4-(α,α-diphenylmethyl)piperidino]-4'-methylvalerophenone hydrochloride |
| 4-(α,α-diphenylmethyl)piperidine | 6-chloro-4'-n-pentoxycaprophenone | 6-[4-(α,α-diphenylmethyl)piperidino]-4'-n-pentoxycaprophenone hydrochloride |
| 4-(α,α-diphenylmethylene)-piperidine | 5-chloro-4'-dimethylaminovalerophenone | 4'-dimethylamino-5-[4-(αα-diphenylmethylene)piperidino]valerophenone dihydrochloride |
| α,α-diphenyl-4-piperidinemethanol | 6-chloro-4'-piperidinocaprophenone | 6-[4-(α-hydroxy-α-phenylbenzyl)piperidino]-4'-piperidinocaprophenone dihydrochloride |

4-(α-hydroxy-α-phenylbenzyl)-α-(p-piperidino-phenyl)-1-piperidinehexanol.

EXAMPLE 11

4'-tert-Butyl-5-[4-(α-hydroxy-α-phenylbenzyl)-piperidino]valerophenone oxime hydrochloride A mixture of 15 g (0.028 mole) of 4'-tert-butyl-5-[4-(α-hydroxy-α-phenylbenzyl)piperidino]valerophenone hydrochloride and 15 g of hydroxylamine hydrochloride in 120 ml of pyridine in heated on a steam bath for about 5 hours after which the pyridine is removed at reduced pressure. The remaining residue is dissolved in methanol and added to excess iced 10% HCl. The resulting solid is filtered, washed with water, and recrystallized from isopropyl alcohol to give 4'-tert-butyl-5-[4-(α-hydroxy-α-phenylbenzyl)piperidino]valerophenone oxime hydrochloride.

EXAMPLE 12

4'-Fluoro-5-[4-(α-hydroxy-α-phenylbenzyl)-piperidino]valerophenone oxime

A mixture of 15 g (0.033 mole) of 4'-fluoro-5-[4-(α-hydroxy-α-phenylbenzyl)piperidino]valerophenone hydrochloride and 15 g of hydroxylamine hydrochloride in 120 ml of pyridine is stirred on a steam bath for about 4 hours then cooled to room temperature. The pyridine is removed at reduced pressure on a steam bath, and the residue is triturated with a dilute sodium hydroxide solution and extracted with chloroform. The chloroform extract is washed with water, dried over magnesium sulfate, filtered and concentrated to a residue which is triturated with hexane. The resulting solid is filtered off and recrystallized from ethanol to give 4'-fluoro-5-[4-(α-hydroxy-α-phenylbenzyl)-piperidino]valerophenone oxime.

EXAMPLE 13

When in the procedure of Example 11 an appropriate amount of the compounds of Examples 3 to 8 is respectively substituted for 4'-tert-butyl-5-[4-(α-hydroxy-α-phenylbenzyl)piperidino]valerophenone hydrochloride, the following compounds are obtained:

5-[4-(α-hydroxy-α-phenylbenzyl)piperidino]-4'-methoxyvalerophenone oxime hydrochloride,
5-[4-(α-hydroxy-α-phenylbenzyl)piperidino]-valerophenone oxime hydrochloride,
4'-tert-butyl-6-[4-(α-hydroxy-α-phenylbenzyl)-piperidino] caprophenone oxime hydrochloride,
4'-tert-butyl-6-[4-(α,α-diphenylmethylene)-piperidino]caprophenone oxime hydrochloride,
6-[4-(α-hydroxy-α-phenylbenzyl)piperidino]-4'-methoxycaprophenone oxime hydrochloride,
5-[4-(α,α-diphenylmethyl)piperidino]-4'-methylvalerophenone oxime hydrochloride,
6-[4-(α,α-diphenylmethyl)piperidino]-4'-n-penoxycaprophenone oxime hydrochloride,
4'-dimethylamino-5-[4-(α,α-diphenylmethylene)-piperidino]valerophenone oxime dihydrochloride, and
6-[4-(α-hydroxy-α-phenylbenzyl)piperidino]-4'-piperidinocaprophenone oxime dihydrochloride.

EXAMPLE 14

4'-Cyclopentyl-6-[4-(α,α-diphenylmethylene)-piperidino]caprophenone hydrochloride When in the procedure of Example 2 appropriate amounts of 4-(α,α-diphenylmethylene)piperidine and 6-chloro-4'-cyclopentylcaprophenone are substituted resepctively for α,α-diphenyl-4-piperidinemethanol and 5-chloro-4'-fluorovalerophenone, 4'-cyclopentyl-6-[4-(α,α-diphenylmethylene)piperidino]caprophenone hydrochloride is obtained.

EXAMPLE 15

α-(p-Cyclopentylphenyl)-4-(α,α-diphenylmethylene)-1-piperidinehexanol

When in the procedure of Example 9 (A) an appropriate amount of 4'-cyclopentyl-6-[4-(α,α-diphenylmethylene)piperidino]caprophenone hydrochloride is substituted for 4'-tert-butyl-5-[4-(α-hydroxy-α-phenylbenzyl)piperidino]valerophenone hydrochloride, α-(p-cyclopentylphenyl)-4-(α ,α-diphenylmethylene)-1-piperidinehexanol is obtained.

EXAMPLE 16

5-[4-(α-Hydroxy-α-phenylbenzyl)piperidino]-4'-piperidinovalerophenone

A mixture of 15.6 g (0.35 mole) of 4'-fluoro-5-[4-(α-hydroxy-α-phenylbenzyl)piperidino]valerophenone, the free base of the compound of Example 2, and a small amount of potassium iodide in 100 ml of piperidine is refluxed for about 22 hours. The unreacted piperidine is removed under vacuum, and the remaining residue is triturated with water. The water is decanted and the residue is dissolved in methanol and then added to a large amount of water. The resulting precipitate is dissolved in a large volume of ether, dried over magnesium sulfate, and filtered. The filtrate is concentrated and cooled yielding a product which is recrystallized from ether to give 5-[4-(α-hydroxy-α-phenylbenzyl)piperidino]-4'-piperidinovalerophenone.

EXAMPLE 17

An illustrative composition for hard gelatin capsules is as follows:

| | |
|---|---|
| (a) 4'-tert-butyl-5-[4-(α-hydroxy-α-phenylbenzyl)piperidino]-valerophenone hydrochloride | 10 mg |
| (b) talc | 5 mg |
| (c) lactose | 100 mg |

The formulation is prepared by passing the dry powders of (a) to (c) through a fine mesh screen and mixing them well. The powder is then filled into hard gelatin capsules at a net fill of 115 mg per capsule.

EXAMPLE 18

An illustrative composition for a tablet is as follows:

| | |
|---|---|
| (a) α-(p-tert-butylphenyl)-4-(α-hydroxy-α-phenylbenzyl)-1-piperidinepentanol | 5 mg |
| (b) starch | 43 mg |
| (c) lactose | 60 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 19

An illustrative composition for an aerosol solution is the following:

| | Weight percent |
|---|---|
| (a) 4'-tert-butyl-5-[4-(α-hydroxy-α-phenylbenzyl)-piperidino]valerophenone oxime hydrochloride | 5.0 |
| (b) ethanol | 35.0 |
| (c) dichlorodifluoromethane | 60.0 |

The materials (a), (b) and (c) are packaged in 15 ml stainless steel containers equipped with a metering valve designed to meter 0.2 gram per dose, an equivalent of 10 mg of novel compound (a).

EXAMPLE 20

An illustrative composition for an aerosol suspension is the following:

| | Weight percent |
|---|---|
| (a) 4'-fluoro-5-[4-(α-hydroxy-α-phenylbenzyl)piperidino]-valerophenone hydrochloride (particle size <10μ) | 20.0 |
| (b) sorbitan trioleate | 0.5 |
| (c) dichlorodifluoromethane | 39.75 |
| (d) dichlorodifluoroethane | 39.75 |

The materials (a) to (d) are packaged in 15 ml stainless steel containers equipped with a metering valve designed to meter 50 mg per dose, an equivalent of 10 mg of novel compound (a).

EXAMPLE 21

An illustrative composition for an injectable suspension is the following 1 ml ampul for an intramuscular injection.

| | Weight percent |
|---|---|
| (a) 5-[4-(α-hydroxy-α-phenylbenzyl)piperidino]valerophenone hydrochloride (particle size <10μ) | 1.0 |
| (b) polyvinyl pyrrolidone (M.W. 25000) | 0.5 |
| (c) lecithin | 0.25 |
| (d) water for injection to make | 100.0 |

The materials (a) to (d) are mixed, homogenized, and filled into 1 ml ampuls which are sealed and autoclaved 20 minutes at 121°C. Each ampul contains 10 mg per ml of novel compound (a).

We claim:

1. A compound selected from a base of the formula

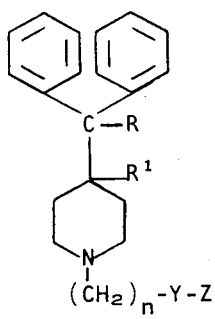

wherein R is selected from hydrogen or hydroxy; $R^1$ is hydrogen; or R and $R^1$ taken together form a second bond between the carbon atoms bearing R and $R^1$; $n$ is the integer 4 or 5; Y is selected from

or

Z is selected from phenyl or a substituted phenyl ring wherein the substituent on the substituted phenyl ring is attached at the ortho, meta, or para position of the phenyl ring and is selected from halogen, a straight or branched alkyl group of from 1 to 6 carbon atoms, an alkoxy group of from 1 to 6 carbon atoms, a cycloalkyl group of from 3 to 6 carbon atoms, a di(lower)alkylamino group, or a saturated monocyclic heterocyclic group selected from pyrrolidino, piperidino, morpholino, or N-(lower)alkylpiperazino; or a pharmaceutically acceptable acid addition salt thereof.

2. A compound of claim 1 wherein R is hydroxy.

3. A compound of claim 2 wherein Y is

4. A compound of claim 3 which is 4'-tert-butyl-5-[4-(α-hydroxy-α-phenylbenzyl)piperidino]valerophenone or a pharmaceutically acceptable acid addition salt thereof.

5. A compound of claim 3 which is 4'-fluoro-5-[4-(α-hydroxy-α-phenylbenzyl)piperidino]valerophenone or a pharmaceutically acceptable acid addition salt thereof.

6. A compound of claim 3 which is 5-[4-(α-hydroxy-α-phenylbenzyl)piperidino]-4'-methoxyvalerophenone or a pharmaceutically acceptable acid addition salt thereof.

7. A compound of claim 3 which is 5-[4-(α-hydroxy-α-phenylbenzyl)piperidino]valerophenone or a pharmaceutically acceptable acid addition salt thereof.

8. A compound of claim 3 which is 4'-tert-butyl-6-[4-(α-hydroxy-α-phenylbenzyl)piperidino]caprophenone or a pharmaceutically acceptable acid addition salt thereof.

9. A compound of claim 3 which is 6-[4-(α-hydroxy-α-phenylbenzyl)piperidino]-4'-methoxycaprophenone or a pharmaceutically acceptable acid addition salt thereof.

10. A compound of claim 3 which is 5-[4-(α-hydroxy-α-phenylbenzyl)piperidino]-4'-piperidinovalerophenone or a pharmaceutically acceptable acid addition salt thereof.

11. A compound of claim 2 wherein Y is

12. A compound of claim 11 which is α-(p-tertbutylphenyl)-4-(α-hydroxy-α-phenylbenzyl)-1-piperidinepentanol or a pharmaceutically acceptable acid addition salt thereof.

13. A compound of claim 11 which is α-(p-anisyl)-4-(α-hydroxy-α-phenylbenzyl)-1-piperidinepentanol or a pharmaceutically acceptable acid addition salt thereof.

14. A compound of claim 1 where R and R¹ taken together form a second bond between the carbon atoms bearing R and R¹.

15. A compound of claim 14 wherein Y is

16. A compound of claim 15 which is 4'-tert-butyl-6-[4-(α,α-diphenylmethylene)piperidino]caprophenone or a pharmaceutically acceptable acid addition salt thereof.

17. A compound of claim 15 which is 4'-cyclopentyl-6-[4-(α,α-diphenylmethylene)piperidino]caprophenone or a pharmaceutically acceptable acid addition salt thereof.

18. A compound of claim 14 wherein Y is

19. A compound of claim 18 which is α-(p-cyclopentylphenyl)-4-(α,α-diphenylmethylene)-1-piperidinehexanol or a pharmaceutically acceptable acid addition salt thereof.

* * * * *